United States Patent
Kanzaki et al.

(10) Patent No.: US 7,829,334 B2
(45) Date of Patent: Nov. 9, 2010

(54) CULTURED MUSCLE CELLS WITH HIGH METABOLIC ACTIVITY AND METHOD FOR PRODUCTION OF THE CULTURED MUSCLE CELLS

(75) Inventors: Makoto Kanzaki, Sendai (JP); Taku Nedachi, Sendai (JP); Hideaki Fujita, Sendai (JP)

(73) Assignee: Tohoku University, Sendai-shi (JP)

( * ) Notice: Subject to any disclaimer, the term of this patent is extended or adjusted under 35 U.S.C. 154(b) by 376 days.

(21) Appl. No.: 11/524,375

(22) Filed: Sep. 21, 2006

(65) Prior Publication Data

US 2008/0299086 A1  Dec. 4, 2008

(51) Int. Cl.
*C12N 5/07* (2010.01)
*C12N 5/071* (2010.01)
*C12N 5/077* (2010.01)

(52) U.S. Cl. .................. 435/377; 435/375; 435/366

(58) Field of Classification Search .................. None
See application file for complete search history.

(56) References Cited

FOREIGN PATENT DOCUMENTS

JP          2005-27501      *    2/2005

OTHER PUBLICATIONS

Thelen et al. "Electrical stimulation of C2C12 myotubes induces contractions and represses thyroid-hormone-dependent transcription of the fast-type sarcoplasmic-reticulum $Ca^{2+}$—ATPase gene". Biochem J. (1997), 321: 845-848.*

* cited by examiner

*Primary Examiner*—Vera Afremova
(74) *Attorney, Agent, or Firm*—Birch, Stewart, Kolasch & Birch, LLP

(57) ABSTRACT

The object of the present invention is to provide a method of preparing excellent cultured muscle cells having high metabolic capacity and insulin responsiveness, and further provide a method for the measurement of sensitive metabolic capacity using the cells. The present invention is a method of preparing myotube cells, comprising a step (1) of culturing myoblast cells, a step (2) of differentiation-inducing the myotube cells into the myoblast cells in a culture medium with a high content of amino acids, and a step (3) of applying an electric pulse to the differentiation-induced myotube cells.

20 Claims, 14 Drawing Sheets

Enlargement of myotube cells by the addition of amino acids

No: Normal DMEM 5 x AA: Medium with a high content of amino acids

Present Method

Prior method

Examination of conditions of an electric pulse

Inhibition of an early signal of insulin by the addition of high glucose

Change of sugar uptake amount in a ground state and the insulin-dependent sugar uptake amount by the addition of glucose with different concentrations in assay buffer after 15 minutes of insulin treatment or non-treatment Structure of Exofacial-Myc-GLUT4-ECFP

CULTURED MUSCLE CELLS WITH HIGH METABOLIC ACTIVITY AND METHOD FOR PRODUCTION OF THE CULTURED MUSCLE CELLS

TECHNICAL FIELD

The present invention relates to a method of preparing myotube cells having high contractile performance and high metabolic capacity, a culture apparatus particularly suitable for use by the method, and a method for the measurement of insulin-dependent sugar uptake using the myotube cells.

Furthermore, the present invention relates to myotube cells having high metabolic capacity and the measurable membrane-translocation activity of a glucose transporter, and a method for the measurement of the membrane-translocation activity of the glucose transporter in an extraneous stimulus-dependent manner such as insulin, etc., using the myotube cells.

BACKGROUND ART

Not only do muscles control motor function, but also play an essential role as the largest insulin target tissue in homeostatic maintenance of blood sugar. In type II diabetes, which is explosively increasing at present, "sugar uptake" into muscles that is dependent on insulin stimulation is significantly waning. Moreover, it is known that suitable motor stimulation effectively improves the clinical condition, and exercise therapy is carried out at clinical sites; however, details of the molecular mechanism are unknown.

Muscular motion, in other words contraction and extension of muscle cells, is associated with a large energy consumption as well as mechanical stimulation. Moreover, the multiple stimulation of both creates "healthy muscle cells" with high glucose metabolic capacity within a living body, and maintains proper insulin responsiveness. However, in a culture system, it is difficult to maintain contractional activity of muscle cells that is sufficiently active, and excellent cultured muscle cells that simulate a living body, particularly ones suitable for research into metabolic capacity, do not exist. Thus, efficacy of a drug for muscle cells, etc., has been evaluated using (1) an animal experiment or muscular tissues collected from animals, or (2) an undeveloped cultured muscle cell strain.

Muscular tissues bring out high metabolic capacity through exercise, hence procedures such as forcing animals to run on a treadmill or swim in a tank for a long time were mainly carried out to evaluate the efficacy of a drug that affects the metabolic capacity of muscle cells when muscular tissue collected from the animal was used. Moreover, electrodes were connected to a muscular tissue collected from an experimental animal to activate contraction with an electric pulse in order to prepare a sample. These animal experiments involve ethical issues, in addition to being unsuitable for screening a number of drugs.

On the other hand, an excellent cultured cell system that simulates a living body helps to screen drugs to a large extent. However, a cultured muscle cell system taking into consideration the characteristics of muscle cells, mainly contraction and extension, is poor, and contractile performance of cultured muscle cells prepared under normal culture conditions has hardly been developed. Therefore, they were not developed enough to have high metabolic capacity as described in Biochem. Pharmacol., 2003, Vol. 65, page 249-257, and Am. J. Physiol. (Endoclinol Metab), 2002, Vol. 283, page E514-524, and they did not simulate the muscles of a living body, making them completely unsuitable for research on metabolic capacity.

Furthermore, in Japanese published unexamined application No. 2005-27501, a method of preparing muscle cells having automatic contractile capacity by applying an electric pulse by wave pulse to myoblast cells is described. Moreover, in Japanese published unexamined application No. 2003-225, a cell culture apparatus that passes a vertical electric current and a cell culture method are described.

However, even with the cell culture methods described in these patents, the preparation of muscle cells suitable for research on metabolic capacity such as uptake measurement, etc., has not been successful. Moreover, the prior measurement conditions of metabolic capacity were not suitable for cultured muscle cells.

As described above, energy necessary for life support and movement of muscles is mostly produced by metabolizing sugar responding to various extraneous stimulations such as insulin, exercise, etc., and incorporated within the cells. Such sugar is transported to cells through a facilitated diffusion glucose (glucose transporter; GLUT) family, of which 13 have been identified so far.

Particularly, increased sugar uptake induced by insulin is physiologically important, and, for example, a large part (70-85%) of blood sugar that increases after a meal is incorporated in muscular tissues by insulin stimulation, and hence, muscular tissues play a very important role in controlling the blood sugar of an entire living body.

Therefore, accurately measuring insulin-dependent sugar uptake activity within muscle cells is essential to applications in a wide variety of industries such as developing drugs that increase insulin sensitivity, finding causes that decrease insulin sensitivity, and providing diagnoses at an early stage of diabetes, etc., as well as applications to the field of basic research.

In muscular tissues and adipose tissues where increased sugar uptake by reacting to insulin is facilitated, GLUT4 that is activated by reacting to insulin stimulation is organ-specifically expressed. GLUT4 is hardly exposed on a cell membrane in the absence of insulin stimulation, but is presented in a state of being incorporated in a vesicle group within a cell.

On the other hand, insulin stimulation can increase the amount of a GLUT4 protein exposed on a surface of a cell membrane by facilitating the transportation of the GLUT4 that is present in this intra-cellular vesicle to the cell membrane. In other words, the increased sugar uptake by insulin is achieved by insulin-dependent translocation of this GLUT4 protein to the cell membrane (membrane translocation of GLUT4). This membrane translocation of the GLUT4 in an insulin-dependent manner is a unique characteristic of the GLUT4 protein that is not observed in other GLUT families.

For the measurement of insulin-dependent sugar uptake activity in muscles, a method of measuring how sugar uptake changes by insulin in the entire muscle has been used with an uptake amount of radioisotope-labeled 2-deoxyglucose as an indicator. However, this method has a disadvantage in that an increased uptake amount of sugar purely reacting to insulin is not easily measured if sugar uptake in a ground state that is occasionally observed in tissues/organs with high basic energy consumption such as the muscles, in other words sugar uptake activity in an insulin-independent manner, is high (Biochem. Pharmacol., 2003, Vol. 65, page 249-257; and Am. J. Physiol. (Endoclinol Metab), 2002, Vol. 283, page E514-524).

Thus, the most suitable method for more accurate measurement of insulin-dependent sugar uptake activity is to accurately measure the amount of insulin-dependent translocation of an GLUT4 to a cell membrane. A method of tracing intracellular altered localization of an intrinsic GLUT4 using a technique such as the western blot method, etc., can be used as well. However, this method has an issue in that an advanced operation that takes time to fractionate a cell extract is needed.

As described above, it is not easy to accurately measure the membrane translocation amount of GLUT4 only, and thus, in a cultured adipose cell strain (3T3L1) with an excellent cultured cell system established, a technique for the measurement of the membrane translocation amount of GLUT4 has been developed by creating a GLUT4 with various types of tags biogenetically transfected be expressed exogenously, etc. (J. Biol. Chem., 2001, Vol. 276 (No. 45), page 42436-42444).

Furthermore, research exists in which sugar uptake promoting activity was examined by differentiating myoblast cells C2C12 expressing a GLUT4 with myc tags and treating them with a drug (European J. Pharmacol., 2000, Vol. 410, page 1-5).

However, for differentiation-type myotube cells formed by the fusion of a plurality of myoblast cells, gene transfection is difficult due to the following reasons, and an excellent cultured muscle cell system in which membrane translocation of GLUT4 reacted to insulin has not existed. These reasons include: (1) myotube cells formed by the fusion of a number of myoblast cells and which are highly differentiated cannot be fully adhered after being separated from a culture dish, and hence, gene transfection by an electroporation method often used for cultured adipose cells that are dispersed once cannot be carried out; and (2) gene transfection into undifferentiated myoblast cells can be carried out by various methods; however, myoblast cells transfected with a foreign gene frequently have a decreased differential ability, and occasionally do not become differentiated enough for myotube cells that are sufficiently developed and have insulin responsiveness. Moreover, even if they become differentiated to a certain degree, expression of the foreign gene may be inhibited, and hence, expression of differentiated myotube cells is not expected.

As a heretofore known technique that carries out highly efficient gene transfection into differentiated myotube cells, a method exists that utilizes an adenovirus vector. However, the adenovirus vector can be transmitted to humans, and therefore, high proficiency of the experimenter and research facility where adenovirus vector is used are essential, making it very difficult to carry it out easily and safely. Moreover, infection of the adenovirus vector itself frequently affects the function of cells, and thus, this method may not be suitable for accurate measurement of insulin responsiveness, etc.

DISCLOSURE OF THE INVENTION

Problems to be Solved by the Invention

The object of the present invention is to provide a method of preparing excellent cultured muscle cells having high metabolic capacity and insulin responsiveness, and further provide a method for the measurement of sensitive metabolic capacity using the cells. Moreover, its purpose is to provide a culture system/culture apparatus that can smoothly translocate such highly-advanced cultured muscle cells intact to an activity evaluation system of a number of drugs.

Moreover, the object of the present invention is to provide cultured muscle cells that are highly suitable for measurement of the membrane-translocation activity of a GLUT4 in an extraneous stimulus-dependent manner such as insulin, etc., and to provide a method for the measurement of the membrane-translocation activity of the GLUT4 using the cells.

Means for Resolving the Problems

The inventor discovered, in culturing myoblast cells, that highly-advanced cultured muscle cells suitable for evaluating metabolic capacity could be prepared by optimizing the conditions of a culture solution (removing nutrition, oxygen and waste matter, etc.) and differentiation-inducing while applying a suitable electric pulse, and thus provided the present invention.

Accordingly, the present invention relates to the following aspects:

1. A method for the preparation of myotube cells, comprising a step (1) of culturing myoblast cells, a step (2) of differentiation-inducing the myoblast cells into the myotube cells in a culture medium with a high content of amino acids, and a step (3) of applying an electric pulse to the differentiation-induced myotube cells.
2. A method according to Claim 1, wherein a content of each amino acid in the culture medium with a high content of amino acids is shown in Table 1.
3. A method according to Claim 1, wherein the electric pulse is applied at 10-50V and 0.001-4 Hz with a pulse breadth of 1-24 ms for 0.5-120 hours.
4. A method according to Claim 3, wherein the electric pulse is applied at 20-40V and 0.1-1 Hz with a pulse breadth of 1-24 ms for 2-24 hours.
5. A method according to any one of Claims 1-4, wherein at least the step (3) is carried out in a culture medium under a high oxygen partial pressure condition.
6. A method according to Claim 5, wherein the high oxygen partial pressure condition is effected by dissolving gas with a high oxygen concentration into the medium.
7. A method according to Claim 1, wherein the step (1) is carried out for 1-6 days and the step (2) is carried out for 3-12 days.
8. A method according to Claim 1, wherein the cells are cultured on elastic substrate.
9. A method according to Claim 8, wherein the elastic substrate has been treated in advance with a cell attachment factor.
10. A method according to Claim 1, wherein the cells are cultured in an insert chamber having a basilar part consisting of elastic semipermeable membrane treated in advance with a cell attachment factor, and the electric pulse is applied with electrodes that are positioned facing in an up-and-down direction.
11. An electric pulse-applying culture apparatus with up-and-down facing electrodes, comprising a lower flat-plate electrode, a well-type culture dish, an insert chamber, a covering body, and an upper electrode.
12. A culture apparatus according to Claim 11, wherein a basilar part of the insert chamber consists of elastic semipermeable membrane treated in advance with a cell attachment factor.
13. A method according to Claim 1 using the apparatus according to Claim 11 or 12.
14. A method for the measurement of sugar uptake in an insulin-dependent manner using the myotube cells prepared by the method according to Claim 1, comprising applying insulin stimulation by culturing the cells in a culture medium containing insulin, culturing the cells in the culture medium further supplemented with sugar, and measuring the sugar uptake.

15. A method according to Claim 14, wherein the cells are cultured in the culture medium containing insulin for 5-20 min and then in the culture medium further supplemented with 10-50 mM of glucose for 10-50 min.
16. A method according to Claim 15, wherein the culture medium used for the measurement and a reaction solution are under a high oxygen partial pressure condition.
17. A method according to Claim 16, wherein the high oxygen partial pressure condition is effected by dissolving gas with a high oxygen concentration into the medium.
18. A method for screening a drug targeting muscle, which utilizes the method according to any one of Claims 14-17.

Furthermore, as a result of keen study, the inventor succeeded in differentiation-inducing a recombinant myoblast cell strain constantly expressing a recombinant GLUT4 having a labeled substance at its extra-cellular site (myc-GLUT4-ECFP: enhanced cyan fluorescent protein; FIG. 10) that has been prepared using genetic engineering, into myotube cells constantly expressing myc-GLUT4-ECFP by co-culturing a wild-type myoblast cell strain at a suitable ratio and showing high insulin responsiveness. Moreover, by using these cultured muscle cells, the inventor discovered that the membrane translocation amount of the GLUT4 in an extraneous stimulus manner such as insulin, etc., could be measured, and thus provided the present invention.

Accordingly, the present invention relates to the following aspects:

19. A differentiation-type culture myotube cell constitutively expressing a recombinant GLUT4 having a labeled substance at its extra-cellular site, which is prepared by co-culturing wild-type myoblast cells and recombinant myoblast cells constitutively expressing said recombinant GLUT4.
20. A differentiation-type culture myotube cell according to Claim 19 having a membrane-translocating activity of the recombinant GLUT4 in an extraneous stimulus-dependent manner.
21. A differentiation-type culture myotube cell according to Claim 19 or 20, wherein a labeled substance is bound to the recombinant GLUT4 also at its intra-cellular site.
22. A differentiation-type culture myotube cell according to Claim 19, wherein the labeled substance is an antigenic epitope.
23. A differentiation-type culture myotube cell according to Claim 19, wherein a ratio of the numbers of wild-type myoblast cells and the recombinant myoblast cells in the co-culture is in a range of 100:1-1:100.
24. A differentiation-type culture myotube cell according to Claim 19, wherein another recombinant myoblast cell transfected with a foreign gene expressing another protein.
25. A differentiation-type culture myotube cell according to Claim 19, wherein the myoblast cell is mouse myoblast strain C2C12.
26. A method for the measurement of a membrane-translocation activity of the recombinant GLUT4 using the differentiation-type culture myotube cell according to Claim 19, comprising fixing the cell and measuring an amount of a labeled substance at an extra-cellular site of the recombinant GLUT4 that is present on a cell surface.
27. A method for the measurement according to Claim 26, wherein the amount of the labeled substance is measured by an immunostaining method with an antibody against said labeled substance.
28. A method for the measurement according to Claim 26 or 27, wherein the differentiation-type culture myotube cell is transplanted into an animal body except human, and taken out after its engraftment for measurement.
29. A method for the measurement of a membrane-translocation activity of the recombinant GLUT4 using the differentiation-type culture myotube cell according to Claim 19, comprising measuring an amount of a labeled substance at an extra-cellular site of the recombinant GLUT4 that is present on a cell surface and incorporated into the cell after once having translocated on the cell surface.
30. A method for the measurement according to Claim 29, wherein the differentiation-type culture myotube cell is cultured in a culture medium containing an antibody against the labeled substance, and an mount of the labeled substance comprised in a cell extract is measured.
31. A method for the measurement according to Claim 29, wherein the amount of the labeled substance is measured using an antigen-antibody reaction with the antibody against the labeled substance.
32. A method for the measurement according to Claim 29, wherein the differentiation-type culture myotube cell is transplanted into an animal body except human, and taken out after its engraftment for measurement.
33. A method for the measurement according to Claim 32, wherein the antibody against the labeled substance is injected into the animal body except human so as to be reacted with the recombinant GLUT4 that is present on the membrane of the engrafted differentiation-type culture myotube cell.
34. A method for the measurement of a membrane-translocating activity of the recombinant GLUT4 in an extraneous stimulus-dependent manner using the method for the measurement of the membrane-translocation activity according to Claim 26 or 29.
35. A method according to Claim 34, comprising applying insulin stimulation by culturing the differentiation-type culture myotube cell in a culture medium containing insulin, and measuring the amount of the labeled substance.
36. A method according to Claim 34, wherein the extraneous stimulus is an electric pulse that is applied at 1-100V and 0.01-10 Hz with a pulse breadth of 0.01-500 ms for 0.5-200 hours.
37. A method according to Claim 34, wherein the extraneous stimulus is applied by administrating insulin into the animal.
38. A method according to Claim 34, wherein the extraneous stimulus is applied by making the animal exercise compulsorily.
39. A method for screening a drug targeting muscle, which utilizes the method for the measurement of the membrane-translocation activity according to Claim 26 or 29.
40. A method for transporting a drug to tissue or organ, comprising transplanting the differentiation-type culture myotube cell according to Claim 19 into an animal except human, and administrating an antibody against the labeled substance, which is combined with a drug, after engraftment of the cell to the tissue or organ.

Effect of the Invention

Myotube cells prepared by the method of the present invention form enlarged myotube cells with a developed muscle structure compared to prior methods, and the percentage of cells having such muscle structure is also increasing. The measurement method of the present invention can measure the uptake activity of sugar reacting to insulin stimulation, which is an indicator to show the increased glucose metabolic capacity, and it is significantly promoted in the myotube cells prepared by the present invention compared to prior cells. Therefore, using the method of the present invention, many highly-developed cultured muscle cells in terms of contractile capacity and metabolic capacity compared to prior cells and the metabolic capacity can be sensitively evaluated using the cells.

Furthermore, desorption of an insert chamber part containing cells of an electric pulse-applying culture apparatus with vertical facing electrodes related to the present invention is easy, and hence, the cells are easily moved to a normal multi-well plate for culturing from the culture apparatus, and this can also be carried out automatically. Thus, by culturing cells using the method of the present invention, smooth translocation to a large-scale activity evaluation system of a drug is possible.

Moreover, with regard to the effect of the present invention, by utilizing a characteristic of muscle cells in which a plurality of myoblast cells are fused together and differentiated into myotube cells, differentiation-type culture myotube cells having high insulin responsiveness (sugar uptake activity responding to insulin stimulation) in which almost 100% of myotube cells are transfected with recombinant GLUT4 genes can be prepared by the above method of co-culturing recombinant myoblast cells and wild-type myoblast cells, making it exponentially safer and easier compared to the prior method using adenovirus.

Furthermore, the expression level of a recombinant protein in myotube cells can be easily changed by changing the co-culture ratio. Moreover, several types of any protein can be easily co-expressed by co-culturing and differentiation-inducing myoblast cells transfected with other foreign genes as third and fourth myoblast cells.

Quantitative analysis of the membrane-translocation activity of a GLUT4 in muscle cells and selective uptake activity into the cells can be carried out using the differentiation-type culture myotube cells prepared by the present invention, and hence, sugar uptake activity, and particularly sugar uptake activity in an extraneous stimulus-dependent manner such as with insulin, etc. (insulin sensitivity), and antihyperglycemic effects by motor stimulation, that were mostly evaluated by increases and decreases in the sugar uptake amount, can be accurately and easily evaluated by the present invention.

Figure 1:
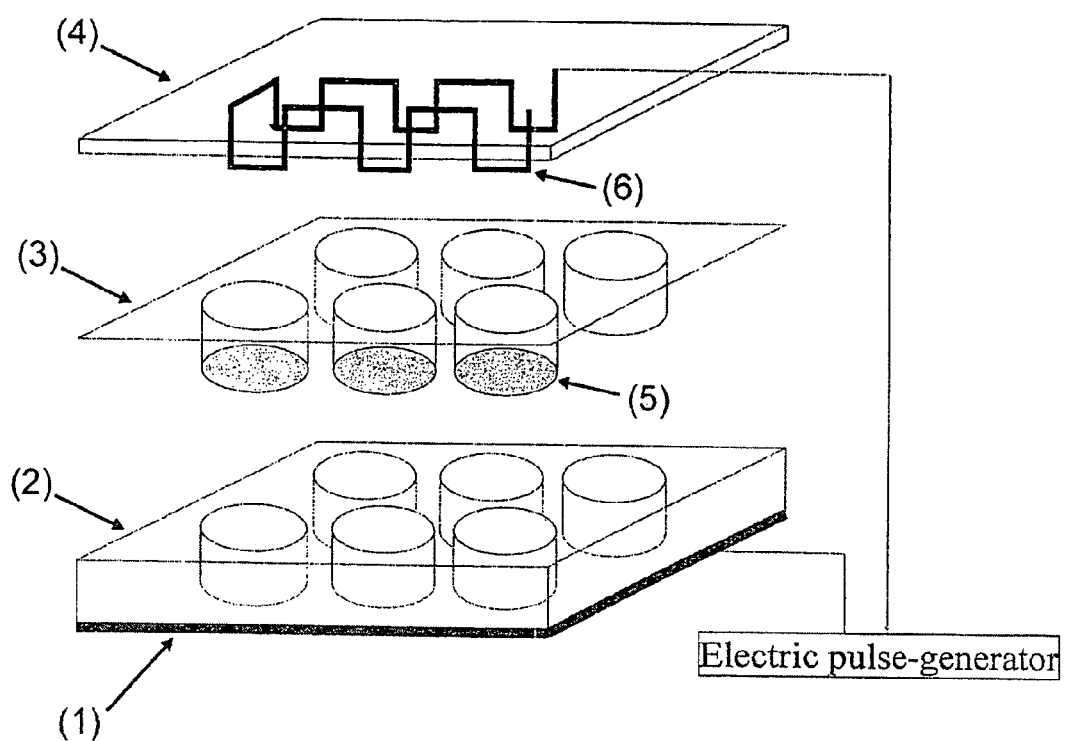
[FIG. 1]
The general structure of a cell culture electrical stimulator according to an illustrative embodiment of the present invention.

DESCRIPTION OF THE NUMERALS (1) Lower flat-plate electrode
(2) Well-type culture dish
(3) Insert chamber
(4) Covering body
(5) Specially-treated semipermeable membrane
(6) Upper electrode Best Mode For Carrying Out The Invention In the method of the present invention for preparing myotube cells, any myotube cells heretofore known by those in the art can be used for "myoblast cells." Although types of animals or tissues that the cells are derived from, etc., are not particularly limited, mammalian cells of primates including human, mice and rats, etc., are preferred, or cells derived from skeletal muscle, smooth muscle, and cardiac muscle, etc., can be used.

Furthermore, any cells turned into a cell strain as "myoblast cells" can be used. Such cell strains include a mouse myoblast strain C2C12 (ATCC No. CRL1772), a myoblast cell strain L6 derived from the skeletal muscle of a rat (ATCC No. CRL1458), a rat cardiac myoblast cell strain H9C2 (ATCC No. CRL1446), etc.

A culture medium used for culturing can be selected from any type heretofore known by those in the art according to the type of cells, etc. For example, a Dulbecco's modified Eagle medium (DMEM culture medium) and a minimum essential medium (MEM culture medium), etc., can be cited. Moreover, these culture mediums may contain various factors accordingly; for example, fetal bovine serum (FBS), albumin, transferrin, hormone, cell growth factor, and vitamins, etc., for the purpose of promoting the proliferation of cells, etc., in the range such that differentiation-inducing of cells is not inhibited.

Normally, culturing is carried out at approximately 1-5× $10^5$ disseminated cells/well, 100% humidity, a cultivation temperature of 37° C., and a culture medium with a pH of approximately 7.2-7.4; however, those in the art may determine other culture conditions accordingly in the normal range.

In the method of the present invention for preparing myotube cells, the first step of culturing myoblast cells is normally carried out for 1-6 days, preferably until the myoblast cells proliferate and become confluent (or dense on the entire surface of the culture vessel). For example, a myoblast cell strain is cultured for approximately 1-6 days until it becomes dense in a DMEM culture medium supplemented with 10-20% fetal bovine serum.

Culture mediums used in the second and third steps are culture mediums with a high content of amino acids. Consequently, differentiation-induction is promoted, removing fatigue of the cultured cells associated with contractional activity by an electric pulse. The content of each amino acid in the culture mediums with a high content of amino acids (mg/l) is approximately 2-5 times the content of essential amino acids in a normal culture medium, and is equivalent to the content supplemented with a nonessential amino acid (L-alanine, L-asparagine, L-asparatic acid, L-glutamic acid, and L-proline) that is not contained in a normal culture medium. Major examples are shown in Table 1 below.

TABLE 1

| Amino Acids | Contents (mg/L) in a normal culture medium (DMEM medium) | Contents (mg/L) in a culture medium with a high content of amino acids |
|---|---|---|
| L-Arg | 84 | 100~600 |
| L-Cys | 62.6 | 80~200 |
| L-His | 42 | 50~250 |
| L-Ile | 105 | 150~350 |
| L-Leu | 105 | 150~350 |
| L-Lys | 146 | 200~500 |
| L-Met | 30 | 45~100 |
| L-Phe | 66 | 90~200 |
| L-Thr | 95 | 125~300 |
| L-Trp | 16 | 20~60 |
| L-Tyr | 103.79 | 125~250 |
| L-Val | 94 | 100~300 |
| L-Ala | 0 | 5~40 |
| L-Asn | 0 | 10~60 |
| L-Asp | 0 | 10~60 |
| L-Gln | 584 | 600~3000 |
| L-Glu | 0 | 10~60 |
| Gly | 30 | 40~80 |
| L-Pro | 0 | 10~60 |
| L-Ser | 42 | 50~100 |

It is preferable to put at least a culture medium used for the third step under a condition of high oxygen partial pressure in order to promote the differentiation-inducing effects of myoblast cells. Moreover, it is preferable to put culture mediums used for all of the steps under a condition of high oxygen partial pressure. Such a condition of high oxygen partial pressure can be provided by dissolving sufficient oxygen, for example, by injecting gas with a high oxygen concentration (95% oxygen, 5% carbon dioxide) into a culture medium for a suitable amount of time before use. Alternatively, a culture medium can be put under a condition of high oxygen partial pressure by carrying out the method of the present invention under a gas atmosphere with a high oxygen concentration. Moreover, it is preferable to replace culture mediums at suitable intervals (for example, every 12-24 hours) in order to supply a source of nutrients and remove waste matter for the purpose of promoting myotube formation.

Furthermore, the bovine serum concentration supplemented in the culture mediums used for the second and third steps is preferably relatively low, for example, in the range of 1-5%. Moreover, a suitable amount (0.5-10 g/l) of sugar such as glucose, etc., can be supplemented for the purpose of supplying nutrition. In addition, various substances that largely influence the differentiation of muscle cells and insulin responsiveness can be supplemented; for example, ascorbic acid, retinoic acid, K252a (a drug that modifies tyrosine kinase activity), agonists/antagonists of a PPAR (a peroxisome proliferater-activated receptor) group, etc.

The second step is normally carried out for 3-12 days, differentiation-inducing myoblast cells into myotube cells. The third step is to apply an electric pulse to the differentiation-induced myotube cells, and such electric pulse is preferably applied at 10-50 V and 0.001-4 Hz with a pulse breadth of 1-24 ms for 0.5-120 hours, more preferably at 20-40 V and 0.1-1 Hz with a pulse breadth of 1-24 ms for 2-24 hours. A membrane voltage-dependent channel of the cells is activated by this electric pulse, and the sarcomere structure of the muscle cells is developed. Moreover, the contractional activity is simultaneously activated to enhance the amount of energy consumption. Furthermore, an apparatus to generate such electric pulse is heretofore known by those in the art. In addition, the electric pulse can be applied horizontally or vertically; however, by utilizing the electric pulse-applying culture apparatus with vertical facing electrodes of the present invention that applies the electric pulse vertically, the prepared myotube cells can be easily translocated to a subsequent system, for example, an activity evaluation system of a drug.

In the process of differentiation-inducing, the cells may be separated from the surface of the culture due to their contractional activity during culturing in order to increase the contractile force of the muscle cells. Thus, it is preferable to culture the cells on an elastic substrate in order to prevent this. For this substrate, any material heretofore known by those in the art that does not affect proliferation of the muscle cells can be used; for example, hydroxyethyl methacrylate (HEMA), polyethylene terephthalate, matrigel, etc. Moreover, considering the operability after culturing, the substrate is preferably in a form that a fluid component such as a semipermeable membrane can permeate through.

Furthermore, it is preferable to treat the substrate in advance with a cell attachment factor (extra-cellular matrix) heretofore known by those in the art, such as collagen, fibronectin, elastin, etc., or an extended-release differentiation-inducing promoting factor, drug, nutrient, etc., in order to promote differentiation-inducing of the muscle cells and cell attachment. This can be carried out by any means heretofore known by those in the art; for example, attaching these substances in advance to the surface of the substrate by soaking the substrate in a solution containing each of these substances, etc. Moreover, the ratio and concentration, etc., of each of the above substances contained in this solution can be selected by those in the art according to the type of cultured cells, type of a culture medium, material of the elastic substrate, etc., and consequently, suitable elasticity can be provided on the surface of the substrate to which the cells attach.

Although the culture apparatus used for the method of the present invention for preparing myotube cells is not particularly limited, an electric pulse-applying culture apparatus with vertical facing electrodes of the present invention having a lower flat-plate electrode, a well-type culture dish, an insert chamber, a covering body, and an upper electrode can be cited as a preferred constitutional example. At this point, it is preferable that the basilar part of the insert chamber inserted between the upper and lower electrodes be comprised of a substrate such as an elastic semipermeable membrane treated in advance with a cell attachment factor. Such a semipermeable membrane itself comprises a material such as polyethylene terephthalate or hydroxyethyl methacrylate (HEMA), etc. Any other components such as an electric pulse generator, etc., can be included.

A general structure of the apparatus of the present invention is shown in FIG. 1. The apparatus of FIG. 1 uses a well-type culture dish (2) having an electroconductive electrode plate (1) placed on the bottom face, and a culture medium for culturing muscle cells is added on this well-type culture dish. Cells are cultured on a treated semipermeable membrane (5) placed on the basilar part in the insert chamber (3) above the well-type culture dish. A suitable electric pulse is applied vertically between the upper electrode placed on a covering body (4) and the lower flat-plate electrode.

The metabolic capacity of muscle cells, particularly sugar uptake activity, has an issue in that it sensitively changes depending on the sugar concentration in a culture solution. In the measurement method of the present invention, in evaluating the metabolic capacity of myotube cells, the above issue is solved by applying insulin stimulation to the cells by culturing in a culture medium containing a suitable amount (for example, approximately 1-1000 nM) of insulin in a prior reaction solution (Krebs-Ringer Phosphate Buffer HEPES: KRPH) for a suitable amount of time (for example, for 5-20 mins), supplying a suitable amount (for example, 10-50 mM, preferably 10-35 mM, and particularly approximately 25 mM) of sugar (for example, glucose), culturing for a limited time (for approximately 10-50 mins), and measuring the metabolic capacity. In other words, it was confirmed that the measurement method of the present invention was a system with which the sugar uptake amount of the ground state decreased and insulin-dependent sugar uptake could be evaluated very well. More specifically, it was indicated that insulin responsiveness observed in the muscle of a living body could be recreated by the measurement method of the present invention. Moreover, in order to sufficiently supply oxygen that is essential for metabolic response, it is preferable to use a culture medium and a reaction solution in the measurement step that have been put under a state of enriched oxygen by the described method. Therefore, for evaluation of metabolic capacity, a prior method of 2-deoxyglucose uptake (Kanzaki M and Pessin J E, J Biol Chem, 2001, Vol. 276, No. 45, page 42436-42444) with the changed above point is used.

The differentiation-type culture myotube cells of the present invention constitutively express a recombinant GLUT4 having a labeled substance at its extra-cellular site, and also show membrane-translocation activity of the recombinant GLUT4 in an extraneous stimulus-dependent manner.

Recombinant myoblast cells that constitutively express a recombinant GLUT4 having a labeled substance at its extra-cellular site can be prepared, for example, according to the method described in Preparation Example 3. At this point, a labeled substance includes any substance heretofore known by those in the art as a substance to label a protein; for example, a substance known as "antigenic epitope (amino-acid sequence)" such as myc, flag, HA, and xpress, etc., and various fluorescent proteins such as "enhanced cyan fluorescent protein."

A base sequence that codes the labeled substance is inserted into a suitable site of a GLUT4 gene to create recombinant genes. For said site, an area exposed to the cell exterior when the GLUT4 is translocated to the cell membrane is preferred; for example, a base sequence equivalent to an extra-cellular exposed area between the first and second penetration sites from the N-terminal, etc. By transforming myoblast cells with expression vectors obtained by linking the recombinant gene prepared by the above method to a suitable vector, recombinant myoblast cells that constitutively express such recombinant GLUT4 having a labeled substance can be created. Moreover, "constitutively express" indicates that the inserted gene is under the control of a "constitutive promoter," and a certain amount of gene products are constantly and substantively produced with no stimulation from outside the cells.

Furthermore, the labeled substance can be bound to the recombinant GLUT4 at an intra-cellular site as well as an extra-cellular site. This enables easy visual confirmation of expression efficiency (expression level of each cell and the number of expressing cells) in the cells of the recombinant GLUT4. Moreover, if the labeled substances bound to the extra-cellular site and intra-cellular site are different, the amount of the recombinant GLUT4 that is present on the cell membrane and in the cell can be separately measured, for example, by using different antibodies from each labeled substance. Furthermore, as an intra-cellular site of the GLUT4 bound to the labeled substance, for example a C-terminal intra-cellular site, can be cited. Therefore, in such cases, the labeled substance can be bound to the intra-cellular site by creating a recombinant gene with a base sequence that codes the labeled substance, induced into the 3'-terminal of the GLUT4 gene.

It is also possible to co-culture by adding recombinant myoblast cells transfected with a foreign gene expressing another protein as well as wild-type myoblast cells and a recombinant GLUT4 having a labeled substance at its extra-cellular site. Consequently, differentiation-type culture myotube cells with co-expression of several types of any protein can be easily created.

A culture medium used for co-culturing can be selected from any type heretofore known by those in the art according to the type of cells, etc. For example, a Dulbecco's modified Eagle medium (DMEM culture medium) and minimum essential medium (MEM culture medium), etc., can be cited. Moreover, these culture mediums can contain various factors accordingly; for example, fetal bovine serum (FBS), albumin, transferrin, hormone, cell growth factor, and vitamins, etc., for the purpose of promoting the proliferation of cells, etc., in the range in which differentiation-inducing of cells is not inhibited.

Normally, co-culturing is carried out at approximately $1\text{-}5\times10^5$ disseminated cells/well, 100% humidity, a cultivation temperature of 37° C., and a cultivation medium pH of approximately pH 7.2-7.4; however, those in the art can determine other culture conditions accordingly in the normal range.

The ratio of the number of wild-type myoblast cells and recombinant myoblast cells in the co-culture can be selected according to the type of myoblast cells, and conditions such as the expression level of a recombinant protein in differentiation-type culture myotube cells prepared in the end, etc.; however, it is normally a ratio of 100:1-1:100.

In regard to co-culturing, firstly, cells are normally proliferated for 1-4 days, preferably until myoblast cells proliferate and become confluent (or dense on the entire surface of the culture vessel). For example, a myoblast cell strain is cultured for approximately 1-4 days until it becomes dense in a DMEM culture medium supplemented with 10-20% fetal bovine serum. Secondly, the myoblast cells are differentiation-induced; however, this can be carried out with the myoblast cell strain with conditions according to a prior method using a DMEM culture medium supplemented with 1-5% bovine serum for approximately 1-20 days. In order to promote a differentiation-inducing effect, a culture medium supplemented with a high amino acid can be used as a culture medium, the environment of the culture is put under a condition of high oxygen partial pressure, and an electric pulse can be applied at 10-50 V and 0.1-10 Hz with a pulse breadth of 0.1-24 ms for 0.5-200 hours.

Furthermore, it is preferable to replace culture mediums at suitable intervals (for example, every 12-24 hours) in order to supply a source of nutrients and remove waste matter for the purpose of promoting myotube formation. In addition, various substances that largely influence the differentiation of muscle cells and insulin responsiveness can be supplemented; for example, ascorbic acid, retinoic acid, K252a (a drug that modifies tyrosine kinase activity), agonists/antagonists of a PPAR (peroxisome proliferater-activated receptor) group, etc.

By the methods described in the above examples 1-10 of the present invention, differentiation-type culture myotube cells can be created by co-culturing.

The measurement method of the present invention is to measure the membrane-translocation activity of a recombinant GLUT4 using the above differentiation-type culture myotube cells. Specifically, for example, it comprises fixing the cells and measuring the amount of a labeled substance at an extra-cellular site of the recombinant GLUT4 that is present on the surface of a cell; in other words, the translocation amount of the recombinant GLUT4 to the cell membrane. In this case, the amount of the recombinant GLUT4 that is present on the cell membrane is measured at a certain point of time. With this method, for example a method heretofore known by those in the art, the amount of a labeled substance can be measured, such as by immunostaining with an antibody against said labeled substance. More specifically, a secondary antibody bound to a fluorescence dye such as rhodamine, etc. is reacted, and the fluorescence amount is measured using a confocal microscope, etc.

Moreover, membrane-translocation activity in the in vivo environment can be measured by transplanting differentiation-type culture myotube cells into the body of a non-human animal (for example, rodents such as mice, rats, etc.), taking them out after a certain period of time after following their engraftment for subsequent measurement.

It is known that a GLUT4 translocated to a cell membrane by extraneous stimulation, etc., subsequently translocates into the cell again. Thus, as another method of measuring membrane-translocation activity of a recombinant GLUT4, the amount of a labeled substance at an extra-cellular site of the recombinant GLUT4 that is present on the surface of a cell and incorporated into the cell after having translocated on the surface of the cell can be measured. In this case, the total amount of the recombinant GLUT4 translocated to the cell membrane within a certain period of time can be measured. With this method or, for example, a method heretofore known by those in the art, the differentiation-type culture myotube cells are cultured in a culture solution containing a suitable amount, for example, 0.01-50.0 µg/ml, of an antibody against the labeled substance, and subsequently the amount of the labeled substance contained in a cell extract can be measured. The amount of the labeled substance can be directly measured using, for example, a liquid scintillation counter or SDS-PAGE if the labeled substance is a radioactive substance, or any method heretofore known by those in the art such as a cellular immunostaining method, ELISA (Enzyme-Linked Immunosorbent Assay), an immunoprecipitation technique, the western blot method, etc.

In this method, the differentiation-type culture myotube cells can be transplanted into the body of the above animal, taken out after a certain period of time after their engraftment for measurement. For example, after their engraftment, the antibody against the labeled substance can be injected into animal blood and reacted with the labeled substance at its extra-cellular site of the recombinant GLUT4 that is present on the membrane of the engrafted differentiation-type culture myotube cells.

Using the above method for the measurement of membrane-translocation activity, membrane-translocation activity of a recombinant GLUT4 in an extraneous stimulus-dependent manner can be measured. In other words, with a suitable method/means heretofore known by those in the art, extraneous stimulation is applied in vitro or in vivo to the differentiation-type culture myotube cell, and subsequently, the amount of a labeled substance, in other words, membrane-translocation activity of the recombinant GLUT4, is measured by the above measurement method. As an extraneous stimulus, for example, chemical substances such as insulin, etc., an electric pulse, exercise, active oxygen, and hypoxic stimulation, etc. can be cited.

Therefore, in measuring the membrane-translocation activity of the recombinant GLUT4 in an extraneous stimulus-dependent manner, for example, insulin stimulation is applied by culturing the differentiation-type culture myotube cells of the present invention in a culture medium containing insulin, a suitable electric pulse is applied by means such as applying an electric pulse, for example, at 1-100 V and 0.01-10 Hz with a pulse breadth of 0.01-500 ms for 0.5-200 hours while the cells are being cultured, or insulin stimulation is applied by administering insulin into an animal.

With each of the above measuring methods using the differentiation-type culture myotube cells of the present invention, the membrane-translocation activity of the recombinant GLUT4, in other words, sugar uptake activity, can be measured. Moreover, the membrane-translocation activity and sugar uptake activity of each recombinant GLUT4 can be measured in an extraneous stimulus-dependent manner.

Thus, using the method of the present invention for the measurement of membrane-translocation activity, screening of a drug targeting muscle (diabetic medicine, insulin sensitizer, sugar uptake enhancer, improving drug for metabolic capacity, differentiation-inducing enhancer, and contraction enhancer, etc.) can be carried out very simply, easily (high throughput), and accurately. Such screening can be carried out by a method heretofore known by those in the art. For example, the measurement of the present invention is carried out in the presence or absence of a chemical substance for a test such as a drug, and in the presence or absence of an extraneous stimulus, and the screening can be carried out by comparing the consequently obtained membrane-translocation activity of the recombinant GLUT4.

Furthermore, by making a suitable adjustment of the blend ratio of myoblast cells expressing a GLUT4 and wild-type myoblast cells or culture conditions, the expression level of the GLUT4 of the cultured muscle cells or the ratio of the expressing myotube cells can be controlled. Therefore, it is possible to track how the effect and efficacy of a drug developed with the screening change according to the expression level of the GLUT4. This is very important considering individual differences in the expression level of the GLUT4 of normal people/patients with metabolic diseases.

EXAMPLES

The present invention is further explained below according to the examples; however, these are only examples of the present invention, and hence, the technical scope of the present invention is not limited to these and any modifications easily thought of by those in the art based on the descriptions of the specifications fall under the scope of the present invention. Moreover, each of the following experiments was carried out using the electric pulse-applying culture apparatus with vertical facing electrodes according to FIG. 1. Furthermore, in the preparation examples, etc., below, culture mediums containing a maximum content of amino acids in the range described in Table 1 were used; however, this was for the purpose of more clearly indicating the effect of containing high amino acids, and the effect specified in the present invention can be obtained with a lesser content of the amino acids than these values.

Preparation Example 1

A mixed solution of collagen (0.1-100 µg/ml), fibronectin (1-100 µg/ml), and a drug (K252a=100 nM) that promotes extra-cellular matrix and differentiation of muscle cells of elastin (1-100 µg/ml) was supplemented on a cellulate semi-permeable membrane in the insert chamber of the above apparatus, and was let to stand at room temperature. Subsequently, the mixed solution was removed from the insert chamber specially-treated as above, and the chamber was washed with Dulbecco's modified phosphate buffered saline several times, and $1\times10^5$ C2C12 cells of a mouse myoblast strain/well (4-well plate) were disseminated.

Figure 2:
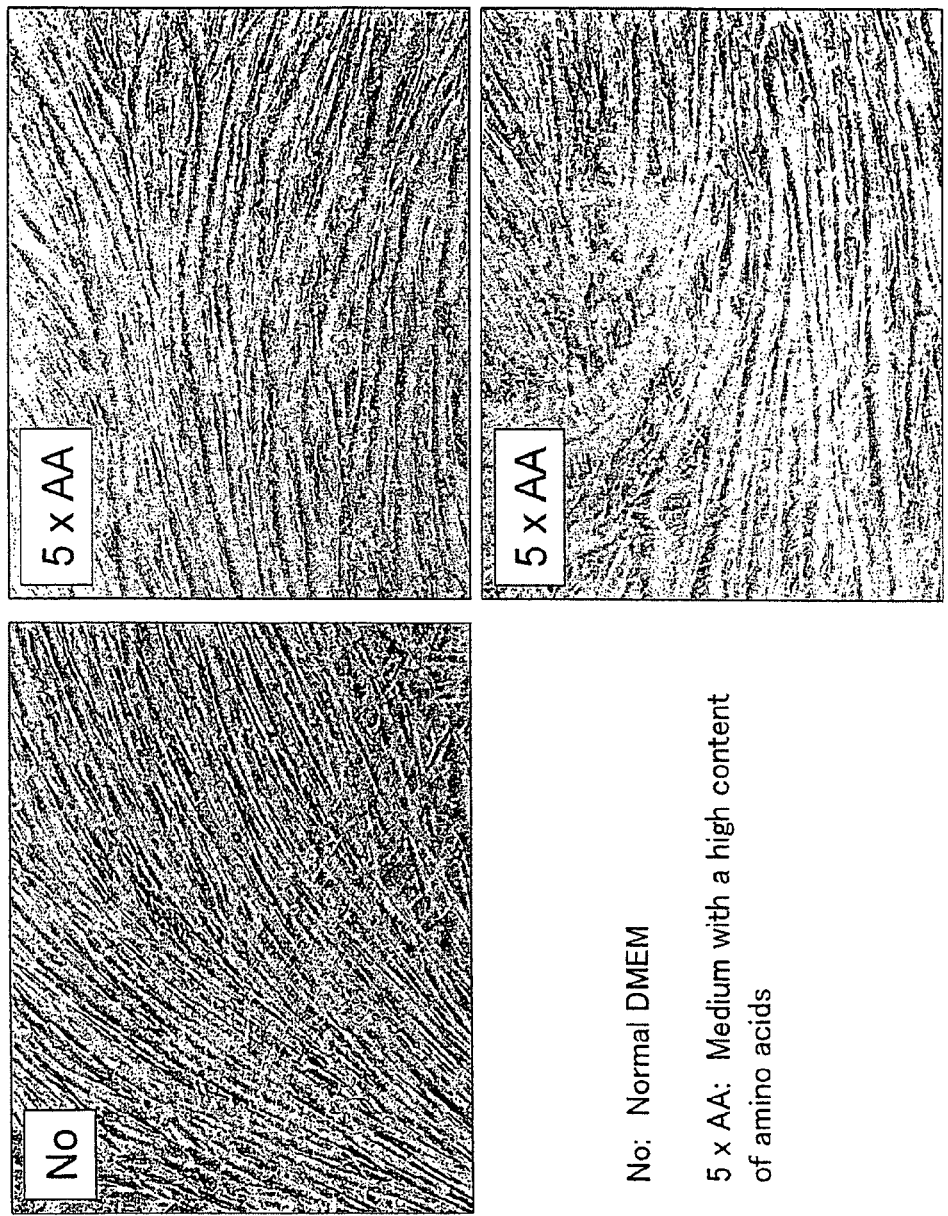
[FIG. 2]
Micrographs (×20) showing a comparison of cultured muscle cells prepared in a normal differentiation-inducing culture medium (DMEM+2% bovine serum) and muscle cells prepared by the method of the present invention.

Subsequently, the C2C12 myoblast cells were cultured for 3 days using a Dulbecco's modified Eagle medium +10% fetal bovine serum until they became confluent. Subsequently, the medium was replaced with a Dulbecco's modified Eagle medium +2% bovine serum for culturing for 8 days, and the cells were differentiated into myotube cells. Moreover, in order to promote constant formation of myotubes and to form enlarged myotubes, the differentiation-inducing culture media were each supplemented with amino acids (maximum content of amino acids in the range described in Table 1), and put under a condition of high oxygen partial pressure effected by directly injecting a mixed gas of 95% $O_2$+5% $CO_2$ into the culture medium. Moreover, the culture media were replaced every 24 hours after differentiation-inducing for the purpose of supplying a source of nutrients and removing waste matter. Consequently, as shown in FIG. 2, it is obvious that the myotube cells were enlarged by using the culture medium with a high content of amino acids (maximum content of amino acids in the range described in Table 1).

Figure 3:
[FIG. 3]
Photos (×60) of cultured muscle cells prepared by a prior method and muscle cells prepared by the method of the present invention, taken with a confocal microscope after the α-actinin molecules were stained.
Figure 3:
Figure 4:
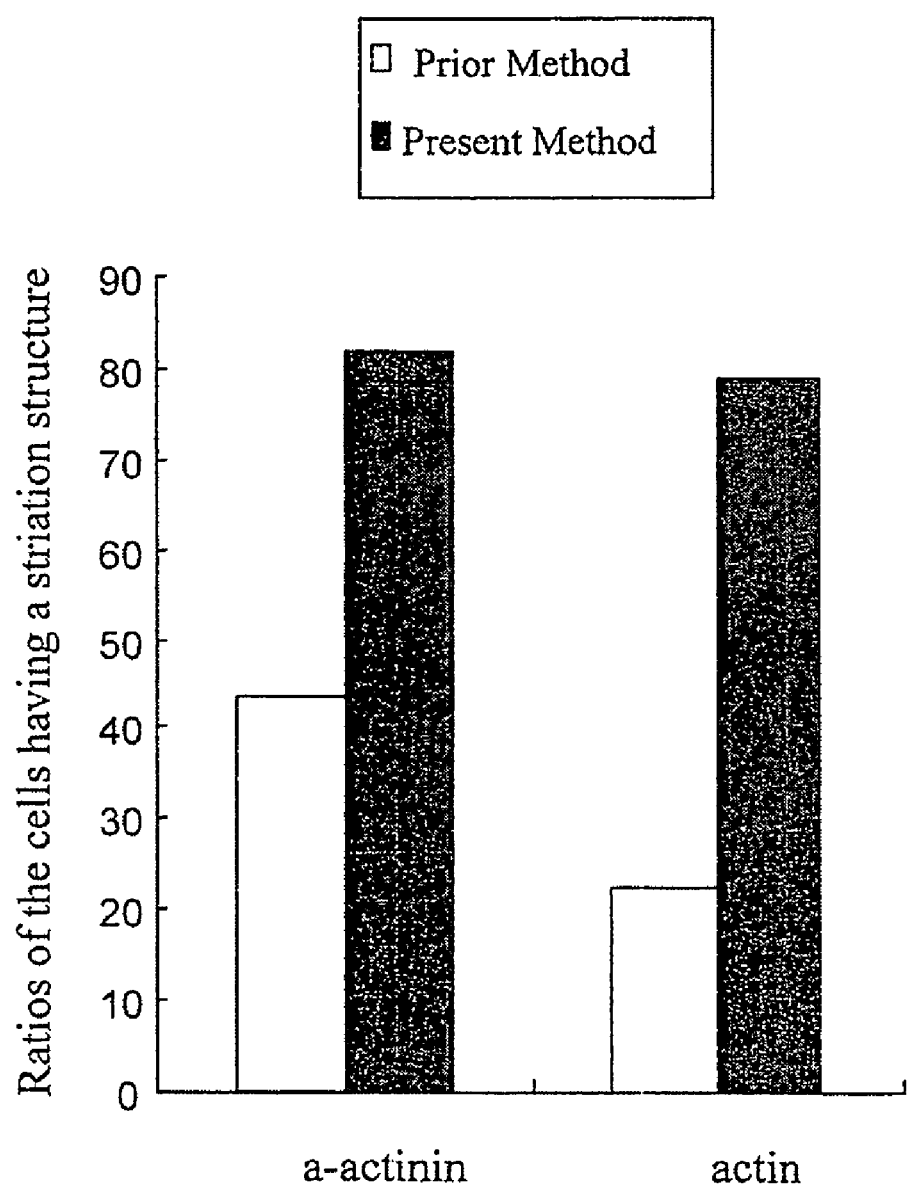
[FIG. 4]
A graph showing ratios of muscle cells having a striation structure in cultured muscle cells prepared by a prior method and muscle cells prepared by the method of the present invention.

An electric pulse (40 V, 1 Hz, 2 ms) was applied for 18 hours to the myotube cells differentiation-induced in the above culture medium with a high content of amino acids with the apparatus of the present invention connected to an electric pulse generator, and development of a sarcomere structure was observed by immunostaining using an α-actinin antibody. It was confirmed that the sarcomere structure was developed by an electric pulse (FIG. 3), and the ratio of the cells having the sarcomere structure was increased (FIG. 4) in the cells differentiation-induced by the method of the present invention compared to the cells differentiation-induced by a prior method (normally differentiation-inducing in DMEM+ 2% bovine serum, no electric pulse applied), with it being obvious that the highly-differentiated myotube cells were significantly increased.

Preparation Example 2

Figure 5:
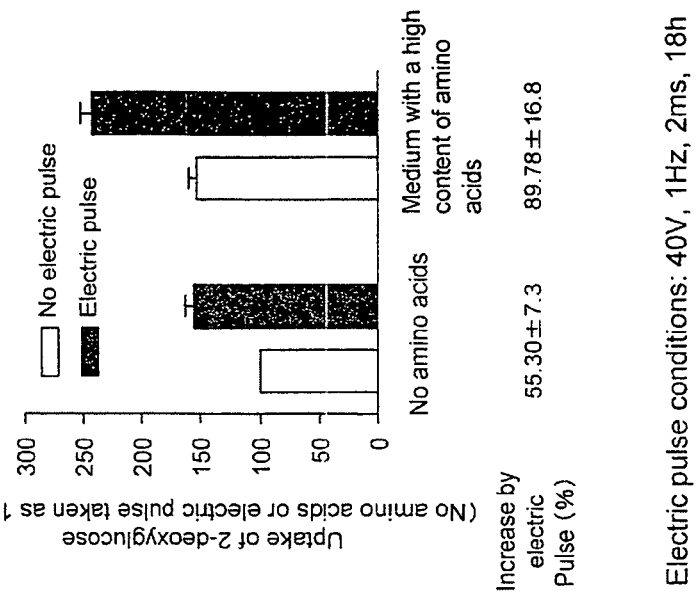
[FIG. 5]
A graph (A) showing an increase in the sugar uptake amount of cells in an electric pulse-dependent manner, in other words, the amount of energy consumption, under the condition of a specific electric pulse. Moreover, it was found that the amount of energy consumption further increased when a culture medium with a high content of amino acids (maximum content of amino acids in the range described in Table 1) was used as a differentiation-inducing culture medium (B).
Figure 5:
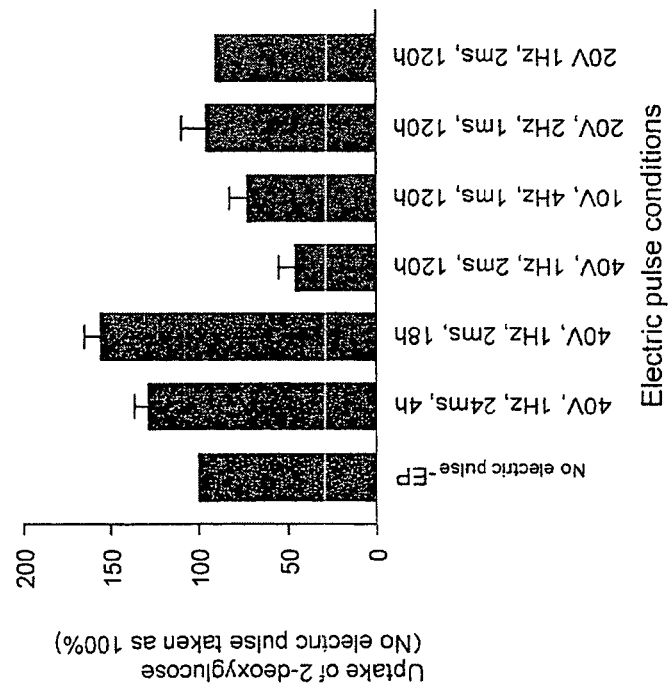

Subsequently, changes in the sugar uptake amount (amount of energy consumption) of the C2C12 cells in applying an electric pulse under various conditions were examined. After the C2C12 myoblast cells that were put in a confluent condition as in Preparation Example 1 were cultured in DMEM+ 2% bovine serum for 8 days, an electric pulse was applied under the various conditions shown in FIG. 5 (A). After the electric pulses were applied, the cells were left at rest on ice to stop the metabolic response, and subsequently, 2-deoxyglucose (0.1 mM, 0.5 uCi/ml) radiolabeled with tritium was incorporated into the cells for 4 minutes, and the total of its uptake amount was measured using a liquid scintillation counter to determine the sugar uptake amount (glucose metabolic capacity) of the cells. Consequently, it was shown that the sugar uptake amount, in other words, amount of energy consumption, of the cells increased in an electric pulse-dependent manner under certain conditions of an electric pulse (FIG. 5A). Moreover, when a culture medium with a high content of amino acids (maximum content of amino acids in the range described in Table 1) was used as a differentiation-inducing culture medium, it was shown that the 2-deoxyglucose uptake amount after an electric pulse was applied was affected (FIG. 5B).

Comparative Example 1

Figure 6:
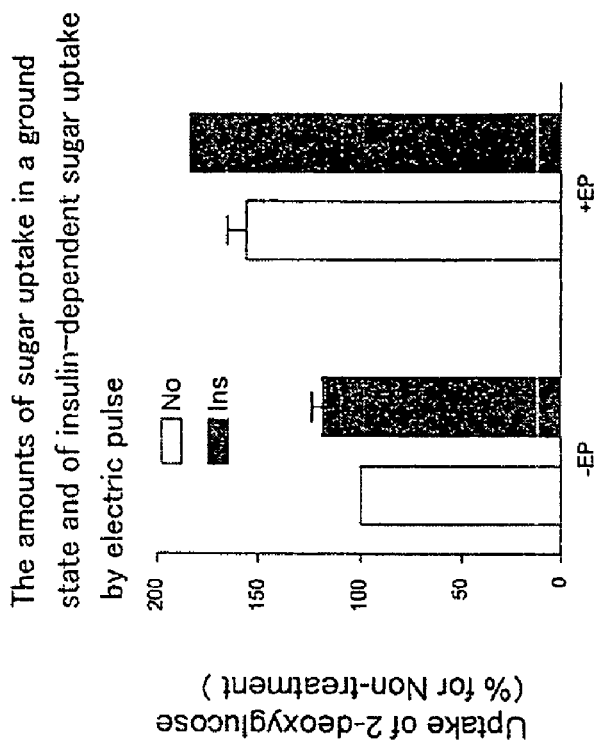
[FIG. 6]
Graphs showing changes in insulin-dependent sugar uptake when only an electric pulse was combined with a differentiation-inducing method.
Figure 6:
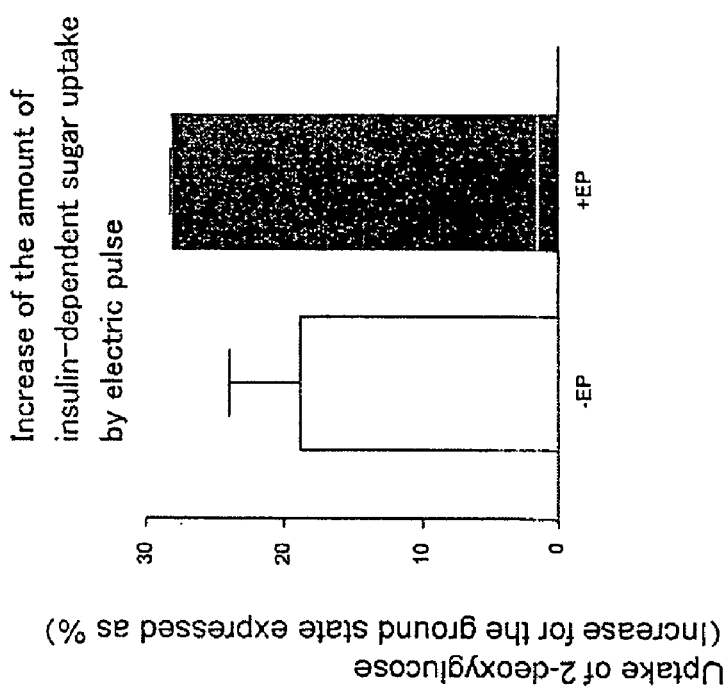

Next, changes in the insulin-dependent sugar uptake when only an electric pulse was combined with a differentiation-inducing method were examined. According to the preparation example, the C2C12 cells were disseminated on a 4-well plate and cultured for 3 days in a normal culture medium (DMEM+10% fetal bovine serum) until they became confluent, and subsequently, they were continued to be cultured for 8 days in a normal differentiation-inducing culture medium (DMEM+2% bovine serum) for differentiation-inducing. Subsequently, after an electric pulse (40 V, 1 Hz, 24 ms, 18 h) was applied, they were treated with insulin for 60 minutes, and the 2-deoxyglucose uptake amount was measured by the above method to evaluate the sugar uptake amount (glucose metabolic capacity) of the cells. Consequently, an electric pulse increased the insulin-dependent sugar uptake amount, but it also increased the sugar uptake amount of the ground state, and hence, it was found to be difficult to observe the increase in sugar metabolism capacity in an insulin-dependent manner in a prior measurement system (FIG. 6).

Comparative Example 2

Figure 7:
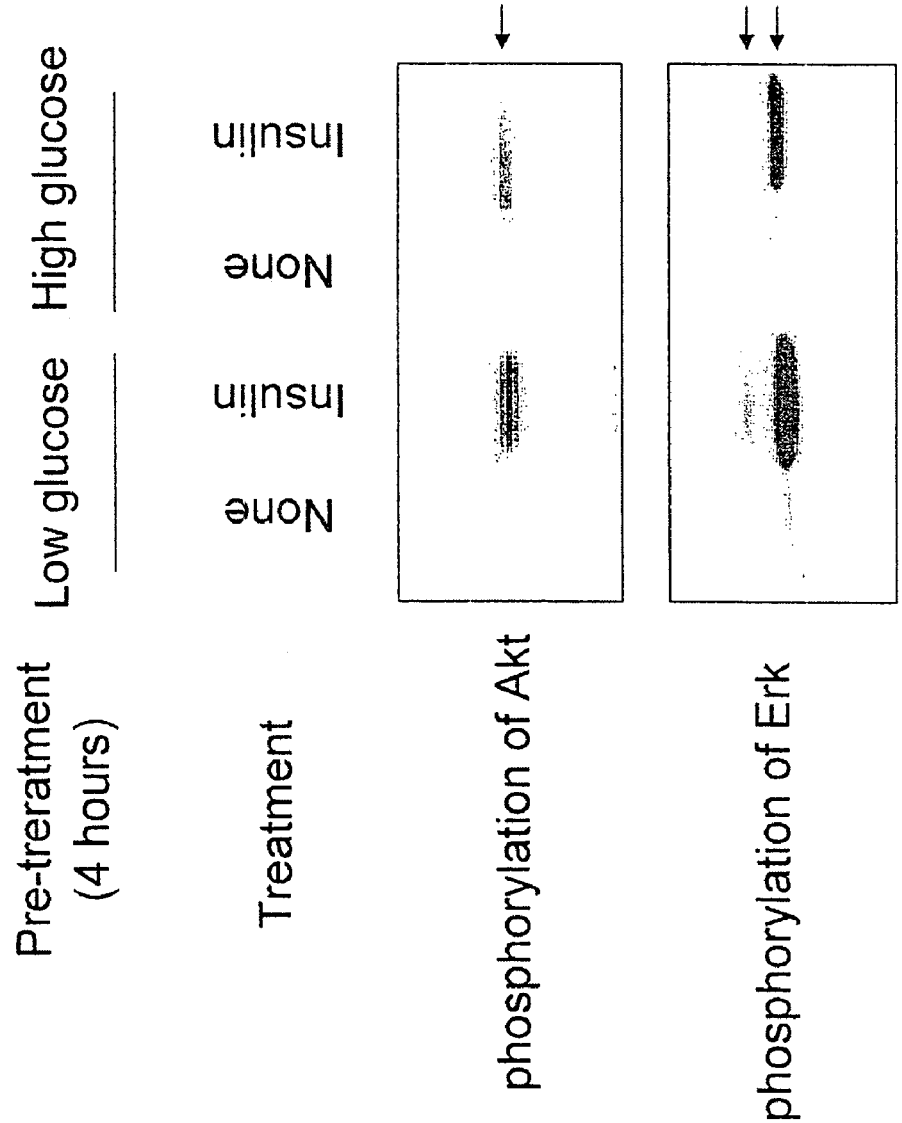
[FIG. 7]
Photos of electrophoresis by western blot analysis showing inhibition of an early signal of insulin (phosphorylation of Akt and Erk) by high glucose treatment.

The C2C12 cells were differentiation-induced as in Comparative Example 1. Next, after they were cultured in a serum-free culture medium (DMEM containing low glucose, 5 mM, or high glucose, 25 mM) for 4 hours, they were treated with insulin for 5 minutes. Subsequently, a cell extract was prepared, western blot analysis was carried out, and insulin signals (phosphorylation of Akt and Erk) were observed. By pre-treating them in high glucose DMEM for 4 hours, it was obvious that the insulin signals were waning (FIG. 7).

Measurement Example 1

Figure 8:
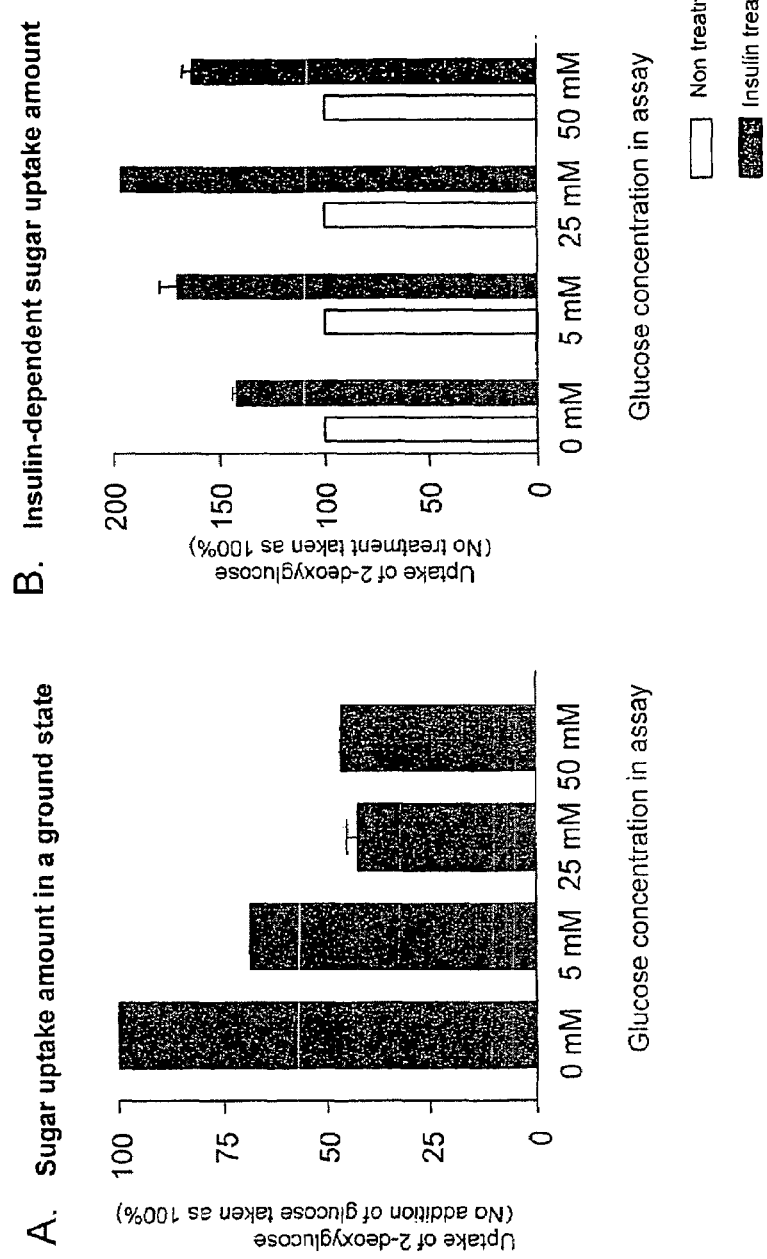
[FIG. 8]
A graph showing changes of sugar uptake amount in a ground state and the insulin-dependent sugar uptake amount in assay buffer with different glucose concentrations regarding C2C12 myotube cells differentiation-induced by the method of the present invention.

After the myotube cells prepared by differentiation-inducing the C2C12 myoblast cells in a serum-free culture medium (DMEM) for 4 hours according to Preparation Example 1, and eliminating the influence of serum hormone, they were stimulated for 15 minutes with insulin with a final concentration of 100 nM dissolved in KRpH (10 mM phosphate buffer, pH 7.6, 1 mM $MgSO_4$, 1 mM $CaCl_2$, 136 mM NaCl, 4.7 mM KCl, 10 mM HEPES, pH 7.6), and subsequently, the culture medium was replaced with KRPH containing 100 nM of insulin and glucose with the intended concentration, and they were treated for 45 more minutes. After the treatment, the metabolic response was stopped by leaving the cell culture chamber at rest on ice, and they were washed 3 times with KRPH under a condition of enriched oxygen. The sugar uptake of the myotube cells was evaluated by incorporating radiolabeled 2-deoxyglucose (0.1 mM, 0.5 uCi/ml) into the cells for 4 minutes, and how much radiation was incorporated into the cells was measured. It was confirmed that by supplementing glucose with a suitable concentration (25 mM) 15 minutes after insulin treatment, the sugar uptake amount in the ground state decreased, creating a system in which insulin-dependent sugar uptake could be evaluated very well. In other words, it was indicated that insulin responsiveness observed in the muscles of a living body could be recreated by the measurement method of the present invention (FIG. 8).

Measurement Comparative Example 1

Figure 9:
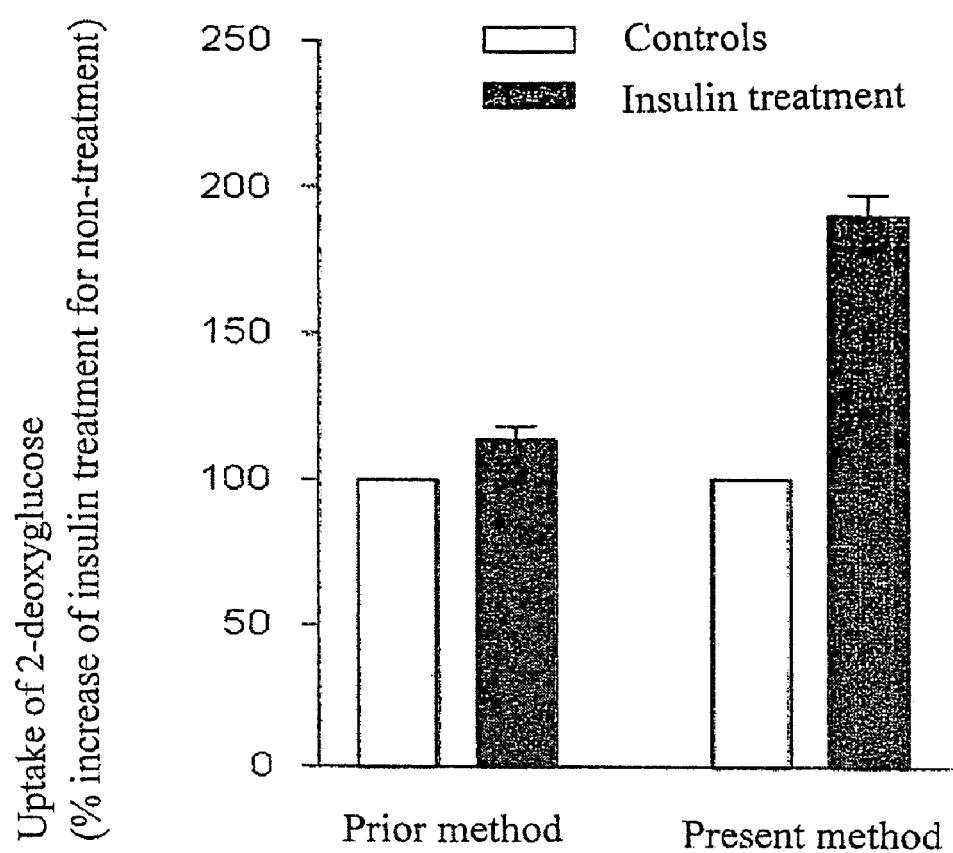
[FIG. 9]
A graph showing a comparison of the insulin-dependent sugar uptake of cultured muscle cells prepared by a prior method and muscle cells prepared by the method of the present invention.
Figure 10:
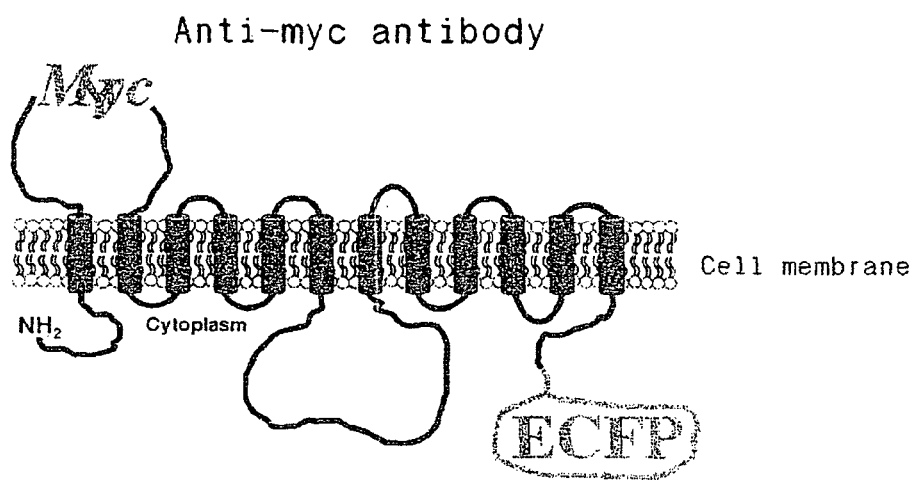
[FIG. 10]
A structure of a GLUT4 having a Myc epitope at its extracellular loop-2 and ECFP at its intra-cellular C-terminal, used for the preparation of the myotube cells constantly expressing GLUT4 by the present invention. It was found that this GLUT4 completely fulfilled the same function as a wild-type GLUT4.
Figure 11:
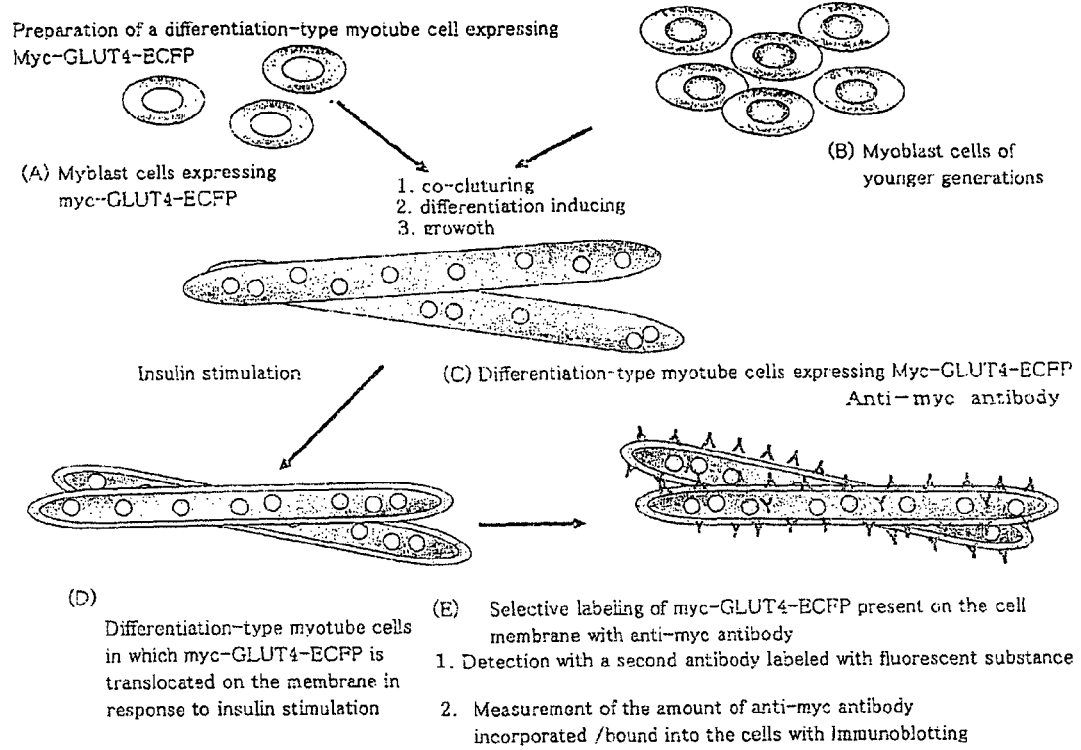
[FIG. 11]
A brief description of an illustrative example of the present invention. Firstly, myotube cells that constantly express myc-GLUT4-ECFP (C) are prepared by co-culturing myoblast cells that constantly express myc-GLUT4-ECFP (A) and wild-type myoblast cells that show high insulin responsiveness by a low passage number (B), and differentiation-induce them. With regard to these cells, the myc-GLUT4-ECFP translocates to a cell membrane along with insulin stimulation (D). By this stimulation, only the myc-GLUT4-ECFP exposed on the cell membrane can be selectively targeted by an anti-c-myc antibody (E). As described above, targeted myc-GLUT4-ECFP can be detected/quantitated by a secondary antibody labeled with fluorescence, etc., under a microscope. Moreover, the amount of an anti-Myc antibody bound to or incorporated into the cells can be measured by immunoblotting.

Furthermore, comparing the insulin-dependent sugar uptake of the cultured muscle cells prepared by a prior method (differentiation-inducing in normal DMEM+2% bovine serum, no electric pulse applied, measurement in KRPH unsupplemented with glucose), and the insulin-dependent sugar uptake of the myotube cells prepared by the method of the present invention (differentiation-inducing in amino acid enhanced and enriched oxygenated DMEM+2% bovine serum, an electric pulse applied at 40 V and 1 Hz with 2 ms for 18 h, measurement in KRPH supplemented with 25 mM of glucose 15 minutes after insulin treatment), it was indicated that the myotube cells prepared by the method of the present invention had the sugar uptake significantly increased by reacting with insulin compared to the prior method, and it was confirmed that the high sugar uptake in an insulin-dependent manner of the myotube cells could be measured by the measurement method of the present invention using the above result (FIG. 9).

Moreover, in the above measurement example and the measurement comparative example, oxygen was directly dissolved in all the culture solutions and the reaction solutions from an oxygen tank (95% $O_2$+5% $CO_2$) for 2 hours.

Preparation Example 3

A GLUT4-ECFP recombinant protein (myc-GLUT4-ECFP) supplemented with a myc tag was prepared as below. Firstly, after a pECFP-myc-GLUT4 was prepared utilizing a myc-GLUT4 insert part of the pcDNA3-myc-GLUT4-EGFP plasmid described in J. Biol. Chem., 2004, Vol. 279, page 30622-30633, it was transfected into pBABE (puromycin-resistant retrovirus preparing vector) described in Nucleic Acids Res., 1990, Vol. 18, page 3587-3496, and pBABE-myc-GLUT4-ECFP was established. The established plasmid was transfected into Plat-E cells, which were retrovirus packaging cells, yielding a retrovirus. After the prepared retrovirus was collected and purified, it was infected into wild-type C2C12 myoblast cells. Subsequently, it was continuously cultured in the presence of 2 μg/ml of puromycin, and over 20 puromycin-resistant C2C12 mutant clones that proliferated from a single cell were isolated. Among these clones, those expressing a suitable amount of an myc-GLUT4-ECFP fusion protein and which were suitable for the purpose were selected using various cell-biological and biochemical techniques, and were used for the following preparation examples.

$2 \times 10^4$ cells/well (6-well plate with a cover glass placed on the bottom face) each of wild-type mouse myoblast strain C2C12 cells (1) and C2C12 myoblast cells (2) expressing the GLUT4-ECFP recombinant protein (myc-GLUT4-ECFP) supplemented with an myc tag, prepared above, were co-disseminated respectively. Subsequently, the myoblast cells were cultured using a Dulbecco's modified Eagle medium +10% fetal bovine serum until they became confluent.

Figure 12:
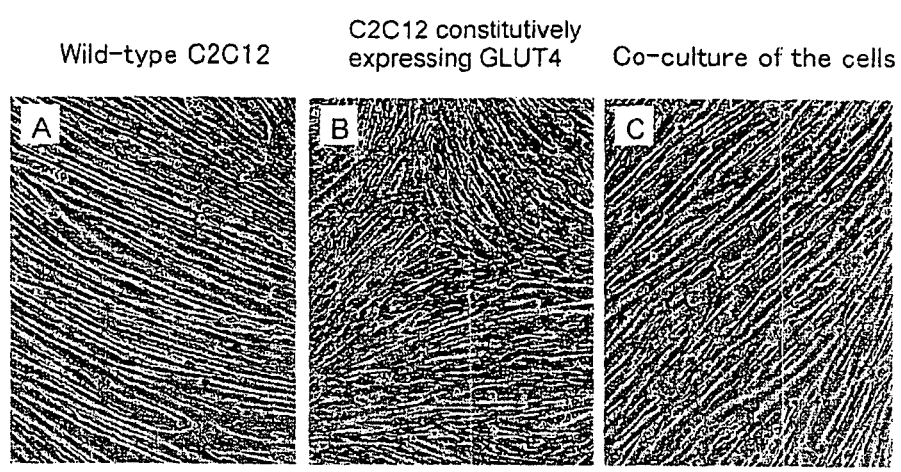
[FIG. 12]
Photos (magnification ratio: ×20) showing the result of the formation of the myotube cells after the wild-type myoblast cells and the myoblast cells that constantly express the myc-GLUT4-ECFP were dependently (A, B) cultured or co-cultured together (C) until they became confluent in DMEN supplemented with 10% fetal bovine serum, and were subsequently differentiation-induced in DMEM supplemented with 2% bovine serum for 6 days.

Next, the cells were moved onto a Dulbecco's modified Eagle medium +2% bovine serum, and cultured for 8 days for differentiation-inducing into myotube cells. Moreover, the culture mediums were replaced every 24 hours after differentiation-inducing for the purpose of supplying a source of nutrients and removing waste matter. Although myotube formation (FIG. 12A) observed in differentiation-inducing wild-type myoblast cells was hardly observed in only the myoblast cells of (2) (FIG. 12B), it was found out that myotube formation was induced by co-culturing (FIG. 12C).

Measurement Example 2

The C2C12 myotube cells (differentiation-type culture myotube cell) expressing a myc-GLUT4-ECFP, prepared according to Preparation Example 3, were stimulated by insulin with a final concentration of 100 nM for 60 minutes. After being washed 3 times with PBS (-), they were fixed by being shaken in PBS (-) supplemented with 2% paraformaldehyde for 15 minutes. After being washed 3 times×10 minutes with PBS (-), they were blocked by being shaken in PBS (-) supplemented with 5% bovine serum for 1 hour. Next, they were shaken for 1 hour using an anti-myc-monoclonal antibody diluted 200-fold with PBS (-) supplemented with 1% bovine serum albumin as a primary antibody. After being washed 5 times×10 minutes with PBS (-), they were shaken for 1 hour using an anti-mice-IgG antibody (The Jackson Laboratory) bound to rhodamine that was diluted 2000-fold with PBS (-) supplemented with 1% bovine serum albumin as a secondary antibody. Subsequently, the glass cover was removed, and they were placed on a glass slide on which Vecta Shield was dropped, and rhodamine and expression of ECFP were observed under a confocal microscope.

Figure 13:
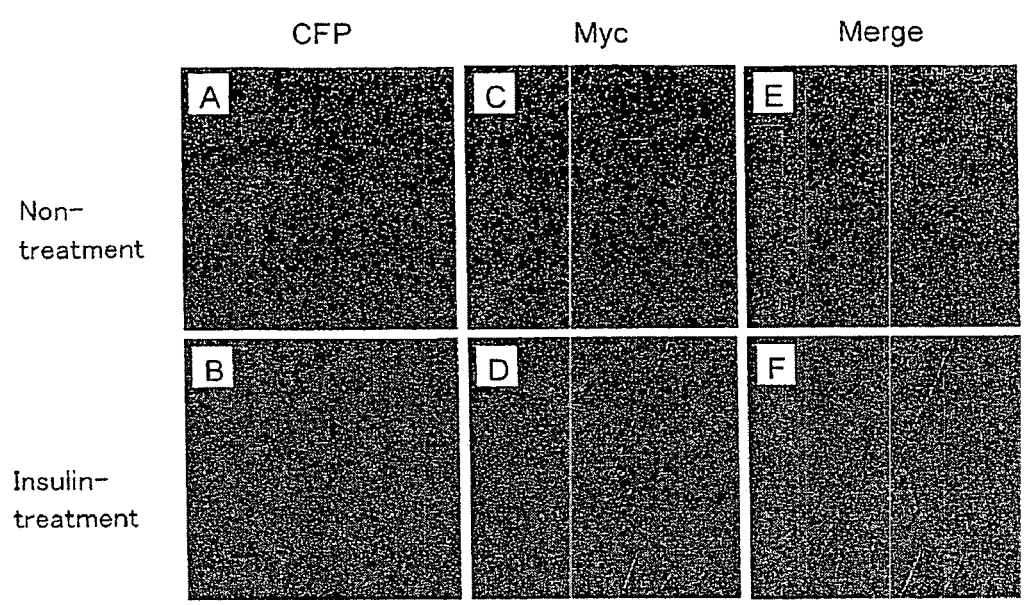
[FIG. 13]
Photos (magnification ratio: ×60) of the observation of fluorescence of rhodamine and ECFP under a confocal microscope, showing expression of a GLUT4 in myotube cells prepared by co-culturing the myoblast cells that constantly express myc-GLUT4-ECFP and wild-type myoblast cells, and the membrane translocation by insulin stimulation.

Consequently, as shown in FIG. 13, expression of ECFP was observed (FIG. 13A), myc on the membrane was not observed (FIG. 13C) in the myotube cells not treated with insulin; however, expression of ECFP (FIG. 13B) and myc on the membrane (FIG. 13D) were both detected in the myotube cells treated with insulin. In other words, it was found that the GLUT4 was translocated on the membrane. Moreover, the fluorescence in simultaneously observing both of the staining is shown in FIGS. 13E and F.

Measurement Example 3

The C2C12 myotube cells expressing a recombinant GLUT4, prepared according to Preparation Example 3, were stimulated by insulin with a final concentration of 100 nM for 60 minutes. After 30 minutes from the start of insulin stimulation, an anti-myc-monoclonal antibody with a final concentration of 4 μg/ml was supplemented in a culture medium. After insulin stimulation, the cells were washed 5 times with PBS (-) to remove anti-myc antibodies that were present on the cell membrane, and subsequently, a cell extract was prepared using Laemmli's buffer. The cell extract was used for 12.5% SDS-PAGE, and western blot analysis using an anti-mice-IgG antibody bound to horseradish peroxidase was carried out. Moreover, detection was carried out using a west super femto detection kit (Pierce Biotechnology Inc.).

Figure 14:
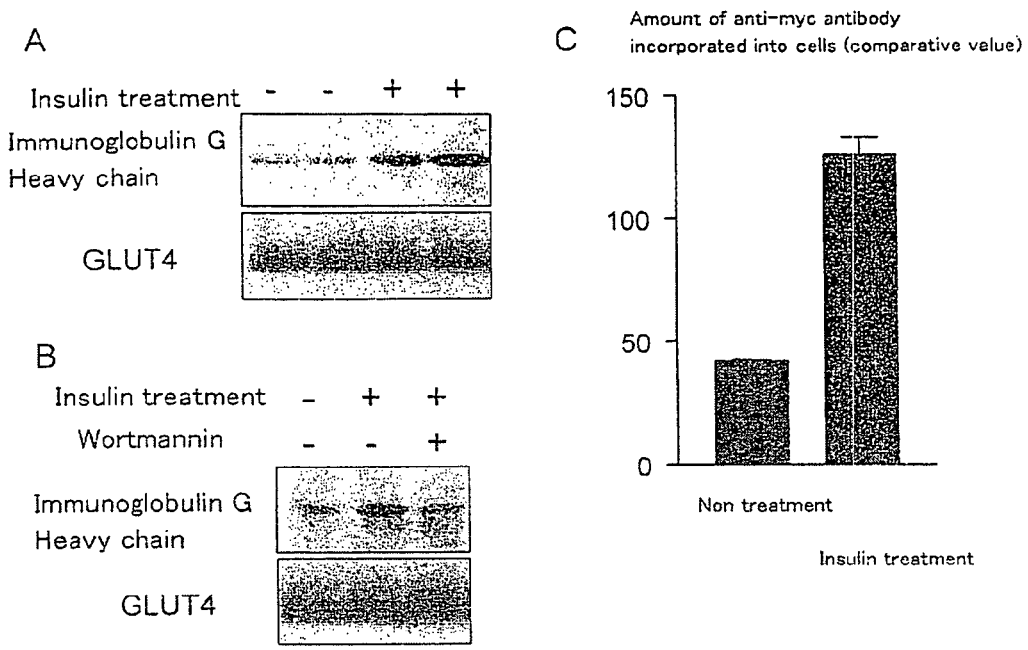
[FIG. 14]
Photos (FIG. 14 A, B) of electrophoresis showing the results of the measurement of GLUT4 activity by insulin stimulation using the myotube cells of the present invention by western blot analysis. Moreover, a graph (C) showing that activity of GLUT4 increases approximately 3-fold in response to insulin.

Consequently, it was found that the amount of the anti-myc antibody incorporated into the cells by insulin stimulation significantly increased (FIG. 14A). It was also found that this effect was inhibited by Wortmannin which inhibited insulin signals (FIG. 14B). Such results of western blot analysis can be easily quantified using known computer software such as NIH image, etc., and in this example, it was found that the GLUT4 activity increased approximately 3-fold by insulin (FIG. 14C).

INDUSTRIAL APPLICABILITY

With the method of the present invention, it became possible to prepare excellent cultured muscle cells having high metabolic capacity and insulin responsiveness, in other words, highly-advanced muscle cells closer to a living body, in a culture system. By utilizing the measurement method of the present invention, screening of various drugs targeting the muscles (diabetic medicines, insulin sensitizers, sugar uptake enhancers, drugs for improving metabolic capacity, differentiation-inducing enhancers, contraction enhancers, etc.) can be carried out in a high-throughput manner, making the screening very easy. Such methods for screening can be carried out by any method heretofore known by those in the art. For example, the measurement of the present invention is carried out in the presence or absence of a drug, and the screening can be carried out by comparing the obtained sugar uptake amount in an insulin-dependent manner, etc.

Furthermore, in the method of the present invention, differentiation and development of cultured muscle cells can be controlled by making suitable adjustments of electric pulses and culture conditions. Therefore, it is possible to arbitrarily prepare cultured muscle cells with differentiation and development (contractile force and contraction pattern, and metabolic capacity) suitable for medical transplantation.

Moreover, the contraction activity of prepared cultured muscle cells can be artificially controlled, making it possible to prepare a condition in which the motor activity of the muscles of a living body is simulated in a culture system. By utilizing the present invention, research (for example, chemical biology, cell biology, biochemistry, and research using biogenetic techniques) that make use of the advantages of cultured cells such as how motor (contraction and extension activity of muscle) stimulation improves insulin resistance in a living body, etc., are possible.

Additionally, using the present invention, the dynamics of a GLUT4 and proteins that form complexes (IRAP, etc.) can be analyzed using, for example, proteomics technology, facilitating the measurement of stability of the GLUT4 and the GLUT4 complex. All of these applications also provide basic information in screening various new drugs targeting the muscles.

Moreover, the contractional activity of differentiation-type culture myotube cells by insulin stimulation and an electric pulse can be artificially controlled, and thus, for example, research (for example, chemical biology, cell biology, biochemistry, and research using biogenetic techniques) that make use of the advantages of cultured cells such as how motor (contraction and extension activity of muscle) stimulation improves insulin resistance in a living body, etc., are possible.

The differentiation-type culture myotube cells of the present invention can be engrafted to rodents such as mice, etc. Hence, it is possible to analyze what kind of drug administration, nutrition administration, or motor stimulation, etc., inhibits membrane-translocation activity of GLUT4 in an insulin-dependent/independent manner in each site of animal muscle, and this basic knowledge provides very important information in considering applications with humans.

Furthermore, all of the matters disclosed in the references cited in the present specification are included in the specification as part of the description of the present specification.

What is claimed is:

1. A method for the preparation of myotube cells 80% of which have a sarcomere structure, comprising
   (1) culturing myoblast cells;
   (2) differentiation-inducing the myoblast cells into the myotube cells in a culture medium with a high content of amino acids, wherein the high content of amino acids comprises about 2-5 times the content of essential amino acids in Dulbecco's Modified Eagle's Medium and further comprises non-essential amino acids; and (3) applying an electric pulse to the differentiation-induced myotube cells to produce said myotube cells, 80% of which have a sarcomere structure.

2. A method according to claim 1, wherein the essential amino acids comprise about 100 to about 600 mg/L of L-arginine, about 80 to about 200 mg/L of L-cysteine, about 50 to about 250 mg/L of L-histidine, about 150 to about 350 mg/L of L-isoleucine, about 150 to about 350 mg/L of L-leucine, about 200 to about 500 mg/L of L-lysine, about 45 to about 100 mg/L of L-methionine, about 90 to about 200 mg/L of L-phenylalanine, about 125 to about 300 mg/L of L-threonine, about 20 to about 60 mg/L of L-tryptophan, about 125 to about 250 mg/L of L-tyrosine, about 100 to about 300 mg/L of L-valine, about 600 to about 3000 mg/L of L-glutamine, about 40 to about 80 mg/L of L-glycine, and about 50 to about 100 mg/L of L-serine and wherein the non-essential amino acids comprise 5 to about 40 mg/L of L-alanine, 10 to about 60 mg/L of L-asparagine, 10 to about 60 mg/L of L-aspartic acid, 10 to about 60 mg/L of L-glutamic acid, and 10 to about 60 mg/L of L-proline.

3. A method according to claim 1, wherein the electric pulse is applied at 10-50 V and 0.001-4 Hz with a pulse breadth of 1-24 ms for 0.5-120 hours.

4. A method according to claim 3, wherein the electric pulse is applied at 20-40 V and 0.1-1 Hz with a pulse breadth of 1-24 ms for 2-24 hours.

5. A method according to claim 1, wherein at least the step (3) is carried out in a culture medium under a high oxygen partial pressure condition.

6. A method according to claim 5, wherein the high oxygen partial pressure condition is effected by dissolving gas with a high oxygen concentration into the medium.

7. A method according to claim 1, wherein the step (1) is carried out for 1-6 days and the step (2) is carried out for 3-12 days.

8. A method according to claim 1, wherein the cells are cultured on elastic substrate.

9. A method according to claim 8, wherein the elastic substrate has been treated in advance with a cell attachment factor.

10. A method according to claim 1, wherein the cells are cultured in an insert chamber having a basilar part consisting of elastic semipermeable membrane treated in advance with a cell attachment factor, and the electric pulse is applied with electrodes that are positioned facing in an up-and-down direction.

11. A method for the preparation of myotube cells, comprising
(1) culturing myoblast cells;
(2) differentiation-inducing the myoblast cells into the myotube cells in a culture medium with a high content of amino acids, wherein the high content of amino acids comprises about 2-5 times the content of essential amino acids in Dulbecco's Modified Eagle's Medium and further comprises non-essential amino acids; and
(3) applying an electric pulse to the differentiation-induced myotube cells to produce said myotube cells, 80% of which have a sarcomere structure.

12. A method according to claim 11, wherein the essential amino acids comprise about 100 to about 600 mg/L of L-arginine, about 80 to about 200 mg/L of L-cysteine, about 50 to about 250 mg/L of L-histidine, about 150 to about 350 mg/L of L-isoleucine, about 150 to about 350 mg/L of L-leucine, about 200 to about 500 mg/L of L-lysine, about 45 to about 100 mg/L of L-methionine, about 90 to about 200 mg/L of L-phenylalanine, about 125 to about 300 mg/L of L-threonine, about 20 to about 60 mg/L of L-tryptophan, about 125 to about 250 mg/L of L-tyrosine, about 100 to about 300 mg/L of L-valine, about 600 to about 3000 mg/L of L-glutamine, about 40 to about 80 mg/L of L-glycine, and about 50 to about 100 mg/L of L-serine and wherein the non-essential amino acids comprise 5 to about 40 mg/L of L-alanine, 10 to about 60 mg/L of L-asparagine, 10 to about 60 mg/L of L-aspartic acid, 10 to about 60 mg/L of L-glutamic acid, and 10 to about 60 mg/L of L-proline.

13. A method according to claim 11, wherein the electric pulse is applied at 10-50 V and 0.001-4 Hz with a pulse breadth of 1-24 ms for 0.5-120 hours.

14. A method according to claim 13, wherein the electric pulse is applied at 20-40 V and 0.1-1 Hz with a pulse breadth of 1-24 ms for 2-24 hours.

15. A method according to claim 11, wherein at least the step (3) is carried out in a culture medium under a high oxygen partial pressure condition.

16. A method according to claim 15, wherein the high oxygen partial pressure condition is effected by dissolving gas with a high oxygen concentration into the medium.

17. A method according to claim 11, wherein the step (1) is carried out for 1-6 days and the step (2) is carried out for 3-12 days.

18. A method according to claim 11, wherein the cells are cultured on elastic substrate.

19. A method according to claim 18, wherein the elastic substrate has been treated in advance with a cell attachment factor.

20. A method according to claim 11, wherein the cells are cultured in an insert chamber having a basilar part consisting of elastic semipermeable membrane treated in advance with a cell attachment factor, and the electric pulse is applied with electrodes that are positioned facing in an up-and-down direction.

* * * * *